United States Patent [19]

Buck et al.

[11] Patent Number: 4,766,249

[45] Date of Patent: * Aug. 23, 1988

[54] METHOD OF CATALYTICALLY HYDROLYZING ALPHA, BETA-UNSATURATED CARBONYL COMPOUNDS

[75] Inventors: Keith T. Buck; Anthony J. Boeing; Joseph E. Dolfini; Jerome Glinka, all of Cincinnati, Ohio

[73] Assignee: Mallinckrodt, Inc., St. Louis, Mo.

[*] Notice: The portion of the term of this patent subsequent to Jun. 16, 2004 has been disclaimed.

[21] Appl. No.: 942,491

[22] Filed: Dec. 24, 1986

Related U.S. Application Data

[63] Continuation-in-part of Ser. No. 856,595, Apr. 25, 1986, Pat. No. 4,673,766.

[51] Int. Cl.$^4$ ............................................. C07C 45/42
[52] U.S. Cl. ................................... 568/433; 568/458
[58] Field of Search .............. 568/426, 433, 435, 437, 568/440, 458

[56] References Cited

PUBLICATIONS

Guthrie et al., "Can. J. Chem.", vol. 62, pp. 1441–1445, (1984).

Primary Examiner—Werren B. Lone
Attorney, Agent, or Firm—Wood, Herron & Evans

[57] ABSTRACT

Alpha, beta-unsaturated carbonyl compounds are hydrolyzed under alkaline conditions in the presence of water to produce additional carbonyl-containing compounds. High yields are obtained when the alkaline catalyst contains hydroxide ion and the pH is maintained in the range of about 11 to about 13.

8 Claims, No Drawings

METHOD OF CATALYTICALLY HYDROLYZING ALPHA, BETA-UNSATURATED CARBONYL COMPOUNDS

RELATED APPLICATION

This is a continuation-in-part of application Ser. No. 856,595, filed Apr. 25, 1986, invented by Keith T. Buck, Anthony J. Boeing and Joseph E. Dolfini, and assigned to the assignee of this application, now U.S. Pat. No. 4,673,766.

BACKGROUND OF THE INVENTION

The retroaldol reaction of cinnamaldehyde is well known. In this reaction, cinnamaldehyde is converted to benzaldehyde and acetaldehyde with various potential side reactions. Recently, for example, an investigation of the kinetics of the retroaldol reaction of cinnamaldehyde has been reported by J. Peter Guthrie, et al, *Can. J. Chem.*, Vol. 62, pp. 1441–1445 (1984). The conversion of the cinnamaldehyde to benzaldehyde has been long known and well studied. However, it has not been heretofore known to produce benzaldehyde from cinnamaldehyde in substantial yields, and favorable reaction conditions for production of such yields have not been reported. Similarly, citral has been hydrolyzed via the retroaldol reaction to produce 6-methyl-5-hepten-2-one and acetaldehyde. Again, however, product yield is low. Up to now, it has not been known how to obtain carbonyl-containing reaction products in substantial yields through the retroaldol hydrolysis of any of the alpha,beta-unsaturated carbonyl compounds, of which cinnamaldehyde and citral are examples.

SUMMARY OF THE INVENTION

The invention disclosed in the above application Ser. No. 856,595 is directed to a method of making benzaldehyde by conversion of cinnamaldehyde in the presence of water with surprisingly high yields heretofore unachieved. The invention involved the dispersion of cinnamaldehyde in water and, in the presence of an effective catalytic amount of hydroxide ion, fractionally steam distilling benzaldehyde from the cinnamaldehyde. The reaction was conducted at a pH on the order of about 11 to about B 13 and, unexpectedly, within this pH range it has been discovered that a substantial conversion of cinnamaldehyde to benzaldehyde could be achieved on the order of about 75% or more. It has also been found that the conversion may be achieved at such a high pH without adverse side reaction.

It has also been found that members of the class of compounds known as alpha,beta-unsaturated carbonyl compounds, of which cinnamaldehyde is an example, can be hydrolyzed via the retroaldol reaction to produce carbonyl-containing compounds in substantial yields.

In a preferred mode of conducting the method, the alpha,beta-unsaturated carbonyl compound is dispersed in water in the presence of shearing agitation. It will be understood that other water soluble or dispersible co-solvents such as alcohols, ethers or the like may be used in the aqueous reaction medium. An anionic surfactant such as sodium lauryl sulfate or a non-ionic surfactant such as polyethylene glycol having a molecular weight in the range of 400 to 600 may be used. Preferably, the hydroxide ion is furnished by means of sodium hydroxide which also achieves a pH in the range of about 11 to about 13. After the starting materials have been charged to the flask, reaction is initiated with the addition of heat. Once reaction has begun, separation of the products is achieved through the production of water-product azeotropes which are isolated by fractional distillation. It has been critically determined that the fractional distillation must be conducted at a pH within the range of about 11 to about 13, preferably about 12 to about 12.5. Reactions conducted outside this pH range exhibit very poor conversion to desired product because side reactions, polymerization and other adverse reactions occur.

Reactions conducted within the pH range of about 11 to about 13, and especially between about 12 and about 12.5, produce significant yields on the order of 75% or greater and are substantially free of side reaction products. These results are considered to be unexpected especially at the high pH levels of the reaction where it may have been expected that side reactions would have significantly lessened or prevented the yield for the desired product.

The reaction products isolated by fractional distillation may be further purified by means of additional separation techniques. The separation technique employed may vary with the degree of purity sought. Pure alpha,beta-unsaturated carbonyl compounds may be used as starting materials for the reaction. However, product yield percentage is not adversely affected when natural products containing the desired starting materials are used in the reaction. Thus, a natural product such as cassia oil containing substantial amounts of cinnamaldehyde may be used successfully in this invention. Similarly, lemon grass oil containing citral may be used successfully. Also, pennyroyal oil may be utilized under the teachings of this invention as a source of pulegone, an alpha,beta-unsaturated carbonyl compound.

DETAILED DESCRIPTION

The method in its broader aspects is practiced by hydrolyzing after dispersing in water an alpha,beta-unsaturated carbonyl compound having the formula

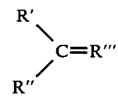

to produce a carbonyl-containing compound and a by-product having the general formulas

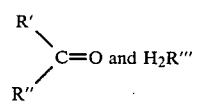

The substituents $R'$ and $R''$ are hydrogen, aliphatic or aromatic hydrocarbon groups or substituted derivatives thereof, and $R'''$ is an aliphatic or aromatic aldehyde- or ketone-containing group having the carbon to oxygen double bond of the aldehyde or ketone conjugated with the alpha,beta double bond between C and $R'''$ of the alpha,beta-unsaturated carbonyl compound. The hydrolysis reaction proceeds under the action of heat and is catalyzed by hydroxide ion having a concentration level sufficient to maintain the solution pH between about 11 and about 13.

A large number of alpha,beta-unsaturated carbonyl compounds may be hydrolyzed according to the teachings of this invention. The compounds in the following non-comprehensive list are included under the description of hydrolyzable alpha,beta-unsaturated carbonyl compounds: cinnamaldehyde to produce benzaldehyde and acetaldehyde; citral to produce 6-methyl-5-hepten-2-one and acetaldehyde; pulegone to produce 3-methylcyclohexanone and acetone; 3-decen-2-one to produce heptanal and acetone; 2-dodecenal to produce decanal and acetaldehyde; 2-heptenal to produce pentanal and acetaldehyde; 2-hexenal to produce butanal and acetaldehyde; ionone to produce cyclocitral and acetone; irone to produce 2,5,6,6-tetramethyl-cyclohex-1-ene-1-carboxaldehyde and acetone; 1-(4-methoxyphenyl)-1-penten-3-one to produce paramethoxybenzaldehyde and methyl ethyl ketone; 5-methyl-3-hexen-2-one to produce isobutyraldehyde and acetone; alpha-methyl-iso-ionone to produce citral and methyl ethyl ketone; 5-methyl-2-phenyl-2-hexenal to produce phenyl acetaldehyde and 3-methylbutanal; 4-phenyl-3-buten-2-one to produce benzaldehyde and acetone; and ortho-methoxy cinnamaldehyde to produce ortho-methoxy benzaldehyde and acetaldehyde.

OPERATING EXAMPLES

The following detailed operating examples illustrate the practice of the invention in its most preferred form, thereby enabling a person of ordinary skill in the art to practice the invention. The principles of this invention, its operating parameters and other obvious modifications thereof will be understood in view of the following detailed procedure.

OPERATING EXAMPLE I

A solution was made up from 38.6 lbs. sodium hydroxide, 4 lbs. sodium lauryl sulfate and 10 liters antifoam agent in 760 gallons of water. The solution was stirred until a homogeneous solution was obtained. Then, 1320 lbs. of cassia oil were placed in a 1150 gallon still. The oil contained approximately 72% by weight of cinnamaldehyde. The still had a pot volume of about 1150 gallons onto which was mounted a 4 foot fractionating column containing 1"×1" ceramic tubes and a water-cooled condenser was thereafter connected in series for condensing the benzaldehyde-water azeotrope.

The above prepared sodium hydroxide solution was then added to the cassia oil and introduced into the pot of the still. The pot was equipped with a stirrer. Using pressurized steam and vigorous stirring, the pot was heated to reflux with a pot temperature of 105° C. Reflux was established with a column head temperature of about 99° C. Once reflux was established, it was continued for about 1 hour. During the course of the conversion of the cinnamaldehyde in the cassia oil to benzaldehyde, pH was monitored and was maintained at about 12 to about 12.5. In the event the pH fell below about 12, sodium hydroxide was added to bring the pH back up to the range of about 12-12.5. After refluxing for about 1 hour, take-off of the water-benzaldehyde azeotrope was initiated. The water-cooled condenser was operated at 100° F. thereby enabling the water-benzaldehyde azeotrope to be condensed and collected in a chilled receiver. The acetaldehyde by-product was principally vaporized at the temperature of the condenser and was taken off as vapor. The distillate consisted principally of benzaldehyde in an amount of about 75% or more with minor amounts of cinnamaldehyde, terpenes, orthomethoxybenzaldehyde and acetaldehyde. The crude benzaldehyde was thus collected in a chilled receiver and, in a continuous feed operation the condensed water was continuously fed back to the still to replace what had been taken off and the distillation of the azeotrope continued. The fractional steam distillation of the crude benzaldehyde continued until about 670 lbs. of crude benzaldehyde was obtained. The crude distillate containing benzaldehyde was then dried under vacuum and fractionally distilled under vacuum of about 29" thereby providing a boiling point for the benzaldehyde at about 70° C. in order to obtain a substantially pure benzaldehyde free from residual terpenes and other impurities.

OPERATING EXAMPLE II

Into a 5-liter, 3-neck flask was charged 1012.5 g of pennyroyal oil, containing a substantial portion of pulegone, 3.5 liters water and 30 g sodium hydroxide having a minimum 90% purity. The initial charge of hydroxide produced a pH of about 12. The pH was monitored during the subsequent reaction, and additional sodium hydroxide was added as needed to maintain a pH of about 12. The flask was equipped with a mechanical stirrer/drive motor apparatus and a fractionating column. After agitation was initiated, heat was applied to the mixture in the flask by means of a heating mantle.

As the agitated mixture of pennyroyal oil, sodium hydroxide and water was heated, the pressure in the flask was maintained at atmospheric by permitting the fractionating column to remain uncapped. At a pot temperature of approximately 100° C. and a head temperature of approximately 56° C., distillation occurs and an azeotropic mixture of 96% acetone and 4% water is collected off the top of the fractionating column. The azeotrope was collected by means of the fractionating column.

The co-distillation of acetone occurred over a period of about six days. Agitation and heating were discontinued when no additional distillate was generated. The oil layer remaining in the flask was separated from the sodium hydroxide solution and then water-washed to remove traces of sodium hydroxide.

The washed oil contained the hydrolysis product 3-methylcyclohexanone (b.p. 168°-9° C.), minor amounts of unhydrolyzed pulegone (b.p. 224° C.), and other trace components attributable to the starting pennyroyal oil. The acetone was subsequently assayed for purity, including a determination of water content. The yield of acetone was approximately 73%.

OPERATING EXAMPLE III

Approximately 500 ml water, 5 g (90% active) sodium hydroxide, and 88 g terpeneless lemon grass oil containing approximately 95% citral were charged into a one-liter round bottom flask. The round bottom flask was equipped additionally with a trap having means of permitting removal of the lower density liquid while recirculating the higher density liquid, a fractionating column, and a means for stirring.

The stirred contents of the flask were heated to reflux by means of a heating mantle. The pH of the contents was set at 12 and maintained at that level during the remainder of the run by addition of sodium hydroxide when necessary. The contents were refluxed for one hour, after which time the steam distillate was slowly collected. The distillate take-off was regulated so that little or no citral distilled over. The distillation was continued until no additional oil was collected.

The oil phase distillate was separated from the steam condensate. The separated oil was then short-path vacuum distilled. The main cut yielded 72 g of the citral hydrolysis product, 6-methyl-5-hepten-2-one. The other reaction product, acetaldehyde, was vented from the flask through the fractionating column during the reaction. The yield of 6-methyl-5-hepten-2-one was approximately 90% under the above conditions.

Thus, by means of practicing the preferred processes listed above, the objectives of this invention are achieved in that desirable products can be obtained in good yield from alpha,beta-unsaturated carbonyl compounds. Pure starting materials may be used, but good results are obtainable even from natural sources of the alpha,beta-unsaturated carbonyl compounds. It is critical to the teachings of this invention that reaction take place in an alkaline hydroxide environment wherein the pH is maintained within a window of about 11 to about 13. Unexpectedly, not only are products obtained in yields exceeding 70 to 75%, but the reaction proceeds with a low level of competitive side reactions, polymerization or other adverse reactions.

Having described this invention and its operating parameters, variations may be achieved without departing from the spirit and scope hereof.

What is claimed is:

1. A method of producing a carbonyl-containing compound which comprises
   hydrolyzing by dispersing in water an alpha,beta-unsaturated carbonyl compound of the formula

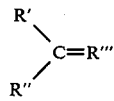

to produce a carbonyl-containing compound and by-product according to the following formulas

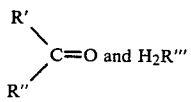

wherein R' and R" are hydrogen, aliphatic or aromatic hydrocarbon groups or substituted derivatives thereof, and R''' is an aliphatic or aromatic aldehyde- or ketone-containing group having the carbon to oxygen double bond of said aldehyde or ketone conjugated with the alpha, beta double bond between C and R''' of said alpha, beta-unsaturated carbonyl compound, and
   conducting said hydrolysis of the alpha,beta-unsaturated carbonyl compound under the action of heat in the presence of a catalytic amount of hydroxide ion and at a pH of about 11 to about 13.

2. The method of claim 1 which is conducted at a pH in the range of about 12 to about 12.5.

3. The method of claim 1 wherein the individual carbonyl-containing compounds obtained from said hydrolysis reaction are fractionally distilled for separation in substantially pure form.

4. The method of claim 1 conducted in the presence of an anionic or non-ionic surfactant.

5. The method of claim 1 conducted under shearing agitation to facilitate the dispersion of the alpha, beta-unsaturated carbonyl compound in the water.

6. The method of claim 1 wherein said alpha, beta-unsaturated carbonyl compound is citral and the carbonyl-containing compounds produced are 6-methyl-5-hepten-2-one and acetaldehyde.

7. The method of claim 1 wherein said alpha,beta-unsaturated carbonyl compound is pulegone and the carbonyl-containing compounds produced are acetone and 3-methylcyclohexanone.

8. A method of producing a carbonyl-containing compound which comprises
   hydrolyzing by dispersing in water under shearing agitation in the presence of an anionic surfactant an alpha, beta-unsaturated carbonyl compound of the formula

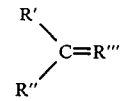

to produce a carbonyl-containing compound and by-product according to the following formulas

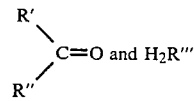

wherein R' and R" are hydrogen, aliphatic or aromatic hydrocarbon groups or substituted derivatives thereof, and R''' is an aliphatic or aromatic aldehyde- or ketone-containing group having the carbon to oxygen double bond of said aldehyde or ketone conjugated with the alpha, beta double bond between C and R''' of said alpha, beta-unsaturated carbonyl compound, and
   conducting said hydrolysis of the alpha, beta-unsaturated carbonyl compound under the action of heat in the presence of a catalytic amount of hydroxide ion and at a pH of about 12 to about 12.5.

* * * * *